(12) United States Patent
Hasumi

(10) Patent No.: US 10,603,427 B2
(45) Date of Patent: Mar. 31, 2020

(54) PACKAGING BODY AND PACKAGING ASSEMBLY

(71) Applicant: TERUMO KABUSHIKI KAISHA, Tokyo (JP)

(72) Inventor: Kiyoaki Hasumi, Yamanashi (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 55 days.

(21) Appl. No.: 15/718,028

(22) Filed: Sep. 28, 2017

(65) Prior Publication Data

US 2018/0015217 A1   Jan. 18, 2018

Related U.S. Application Data

(63) Continuation of application No. PCT/JP2016/060351, filed on Mar. 30, 2016.

(30) Foreign Application Priority Data

Mar. 30, 2015 (JP) .................................. 2015-069233

(51) Int. Cl.
*A61M 5/00* (2006.01)
*B65D 75/36* (2006.01)
(Continued)

(52) U.S. Cl.
CPC .............. *A61M 5/002* (2013.01); *A61M 5/00* (2013.01); *A61M 5/326* (2013.01); *B65D 75/36* (2013.01);
(Continued)

(58) Field of Classification Search
CPC ...... A61M 5/002; A61M 5/00; A61M 5/3137; A61M 5/31511; A61M 2005/3247; A61M 2005/3264; B65D 75/36; B65D 75/366
(Continued)

(56) References Cited

U.S. PATENT DOCUMENTS 2,955,705 A * 10/1960 Krueger, Sr. ......... A61M 5/002
                                                         206/365
5,078,267 A *  1/1992 Wright .................. A61M 5/002
                                                         206/364
(Continued)

FOREIGN PATENT DOCUMENTS

| JP | 2004-035024 | 2/2004 |
|----|-------------|--------|
| JP | 2013-180130 | 9/2013 |
| JP | 2014-162532 | 9/2014 |

OTHER PUBLICATIONS

International Search Report issued in International Patent Application No. PCT/JP2016/060351 dated Jun. 21, 2016.

*Primary Examiner* — Chun Hoi Cheung
(74) *Attorney, Agent, or Firm* — Foley & Lardner LLP

(57) ABSTRACT

A packaging body is configured to house a prefilled syringe that comprises an outer cylinder fillable with a liquid and a plunger movable with respect to the outer cylinder. The packaging body includes a container comprising a housing portion configured to house the prefilled syringe. The housing portion is configured to house the prefilled syringes with various protrusion lengths of the plungers from the outer cylinders, and comprises a first regulating portion that regulates movement of the plunger in a distal end direction in a housed state in which the prefilled syringe is housed in the housing portion.

9 Claims, 7 Drawing Sheets

(51) Int. Cl.
*A61M 5/32* (2006.01)
*A61M 5/31* (2006.01)
*A61M 5/315* (2006.01)

(52) U.S. Cl.
CPC ......... *B65D 75/366* (2013.01); *A61M 5/3137* (2013.01); *A61M 5/31511* (2013.01); *A61M 2005/3247* (2013.01); *A61M 2005/3264* (2013.01)

(58) Field of Classification Search
USPC ............................... 206/364, 570, 571, 438
See application file for complete search history.

(56) References Cited

U.S. PATENT DOCUMENTS

| | | | | |
|---|---|---|---|---|
| 5,772,031 | A * | 6/1998 | Landis | A61B 50/30 206/363 |
| 6,228,324 | B1 * | 5/2001 | Hasegawa | A61L 2/208 206/364 |
| 7,597,196 | B2 * | 10/2009 | Langone | A61M 5/002 206/364 |
| 9,808,570 | B2 * | 11/2017 | Head | A61M 5/002 |
| 10,172,682 | B2 * | 1/2019 | Van Der Raad-Meijer | A61B 50/33 |
| 2013/0062245 | A1 * | 3/2013 | Folchini | A61M 5/002 206/571 |
| 2014/0078854 | A1 | 3/2014 | Head et al. | |
| 2015/0129442 | A1 * | 5/2015 | Head | A61M 5/002 206/366 |

* cited by examiner

PACKAGING BODY AND PACKAGING ASSEMBLY

CROSS-REFERENCE TO RELATED APPLICATIONS

The present application is a bypass continuation of PCT Application No. PCT/JP2016/060351, filed on Mar. 30, 2016, which claims priority to Japanese Application No. 2015-069233 filed on Mar. 30, 2015. The contents of these applications are hereby incorporated by reference in their entireties.

BACKGROUND

The present application relates to a packaging body and a packaging assembly.

A prefilled syringe obtained by aseptically filling a sterilized syringe with a drug solution is known. The prefilled syringe includes an outer cylinder, a gasket capable of sliding in the outer cylinder, and a plunger connected to the gasket and operating to move the gasket, and houses a drug solution in a space surrounded by the outer cylinder and the gasket. In addition, a flange-shaped finger rest is formed at a proximal end of the plunger such that the plunger is operated to move in a distal end direction by pressing this finger rest with a finger or the like.

Such a prefilled syringe is contained in, for example, a blister packaging body described in JP 2004-35024 A or the like. Accordingly, it is possible to protect the prefilled syringe at the time of transportation, to inhibit moisture transpiration of the drug solution from the prefilled syringe, and to maintain a sterile state around the prefilled syringe. When using the prefilled syringe, the prefilled syringe is taken out of the packaging body.

In the conventional blister packaging body, however, a protrusion length of the plunger from the outer cylinder, that is, a position of the finger rest of the plunger with respect to the outer cylinder differs, for example, depending on the amount of a drug solution housed therein, and thus, it is necessary to prepare the blister packaging body for use in accordance with the protrusion length of the plunger.

SUMMARY

An object of certain embodiments described in this application is to provide a packaging body and a packaging assembly capable of housing prefilled syringes with plungers having different protrusion lengths from outer cylinders.

In one embodiment, a packaging body is configured to house a prefilled syringe having an outer cylinder fillable with a liquid and a plunger movable with respect to the outer cylinder. The packaging body includes: a container having a housing portion that houses the prefilled syringe. The housing portion is capable of housing the prefilled syringes with various protrusion lengths of the plungers from the outer cylinders, and has a first regulating portion that regulates movement of the plunger in a distal end direction in a housed state where the prefilled syringe is housed in the housing portion.

In one aspect, the plunger has a first finger rest at a proximal end portion thereof. The housing portion has an elongated shape. The housing portion has a first finger rest housing portion to house the first finger rest. A length of a space of the first finger rest housing portion capable of housing the first finger rest in a longitudinal direction of the housing portion is longer than a thickness of the first finger rest.

In one aspect, the first regulating portion has a plurality of convex portions arranged along the longitudinal direction. The first finger rest is arranged between the two adjacent convex portions in the housed state.

In one aspect, the first finger rest has a concave portion. The first finger rest is arranged between the two adjacent convex portions or a predetermined convex portion among the plurality of convex portions is inserted into the concave portion in the housed state.

In one aspect, a length of a space between the two adjacent convex portions in the longitudinal direction is longer than the thickness of the first finger rest.

In one aspect, the first finger rest has a concave portion. The first regulating portion has a plurality of convex portions arranged along the longitudinal direction. A predetermined convex portion among the plurality of convex portions is inserted into the concave portion in the housed state.

In one aspect, the prefilled syringe has a member movable with respect to the plunger. The housing portion has a second regulating portion that regulates movement of the member in the distal end direction and a proximal end direction in the housed state.

In one aspect, the member has a second finger rest. The housing portion includes a second finger rest housing portion that houses the second finger rest and has the second regulating portion.

In one aspect, the packaging body further includes a sealing member that seals an inside of the housing portion.

In another embodiment, a packaging assembly includes: the packaging body according to any of the embodiments or aspects described above, and the prefilled syringe housed in the housing portion.

According to certain embodiments described in this application, it is possible to house each of a plurality of prefilled syringes whose plungers have different protrusion lengths from outer cylinders. Accordingly, it is unnecessary to prepare a dedicated packaging body in accordance with the protrusion length of the plunger so that labor is saved, which is economical.

DETAILED DESCRIPTION

Hereinafter, embodiments of a packaging body and a packaging assembly will be described in detail with reference to the accompanying drawings.

Figure 1:
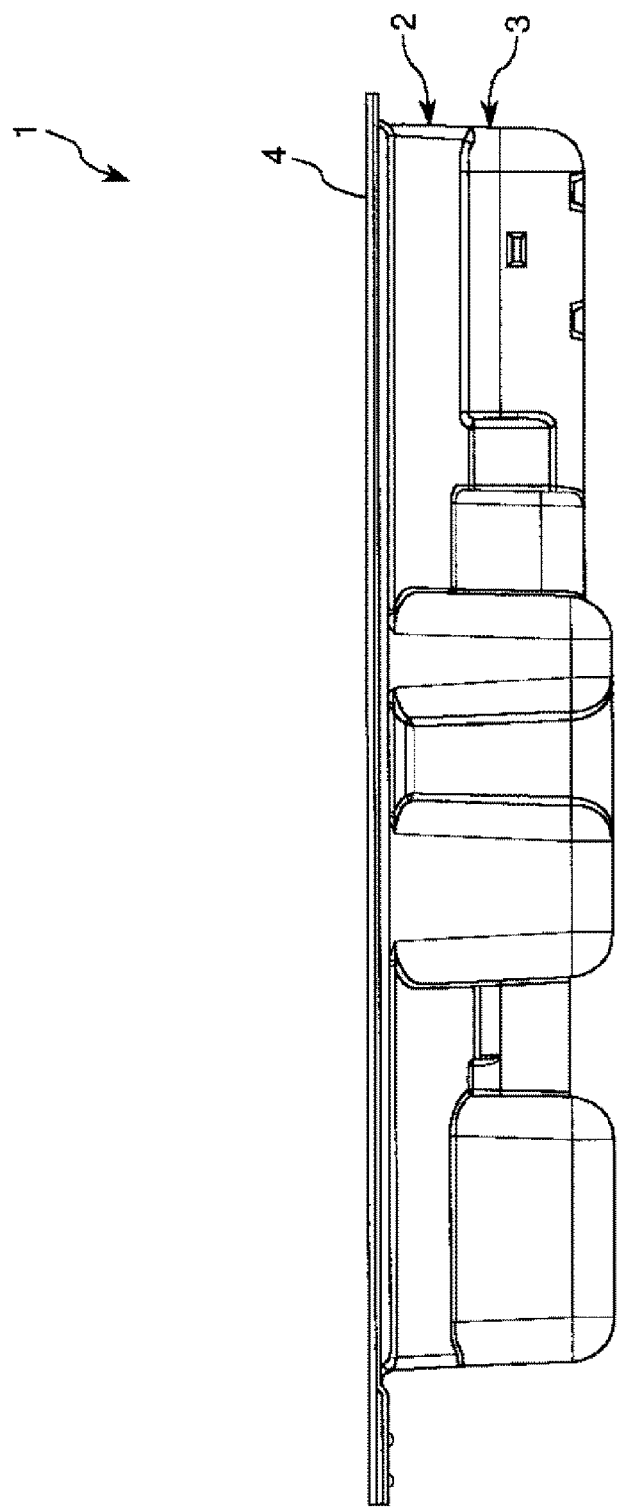
FIG. 1 is a side view illustrating an embodiment of a packaging assembly of the present invention.
Figure 2:
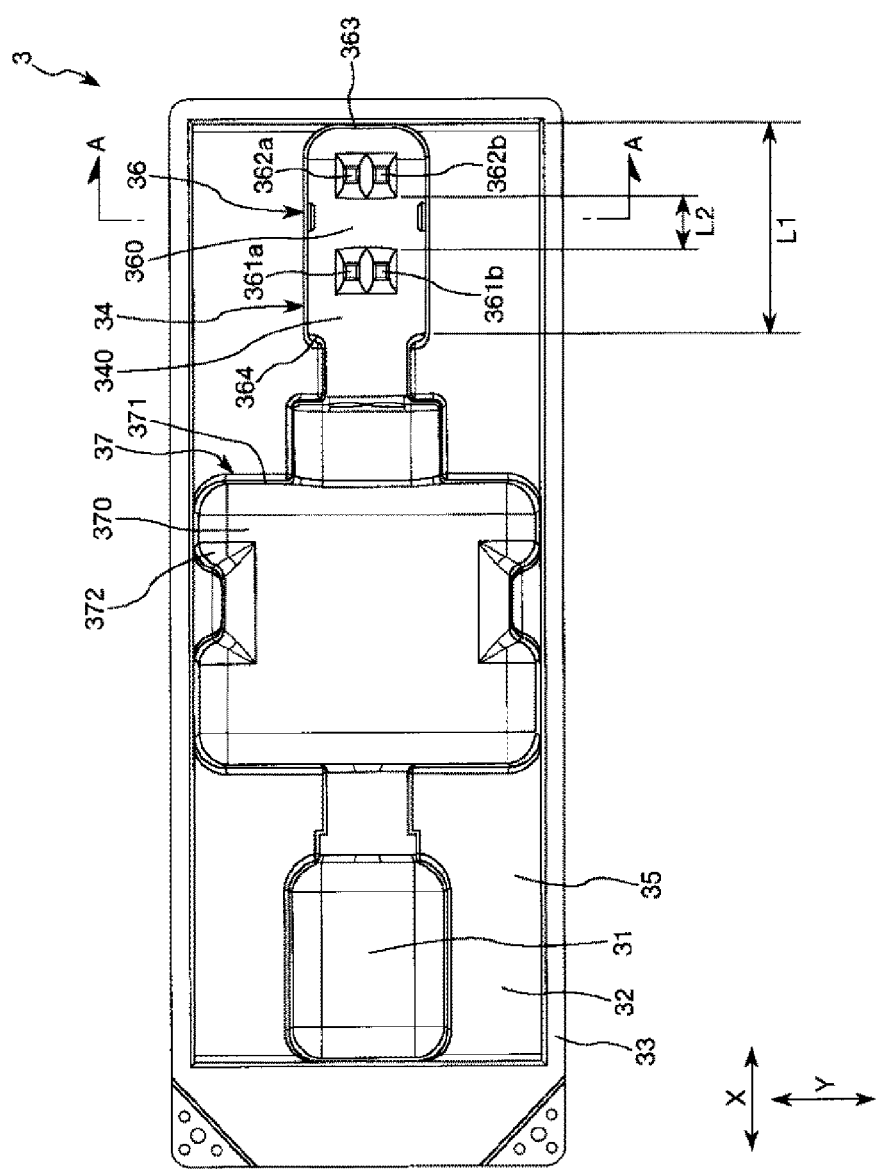
FIG. 2 is a plan view of a container of the packaging assembly illustrated in FIG. 1.
Figure 3:
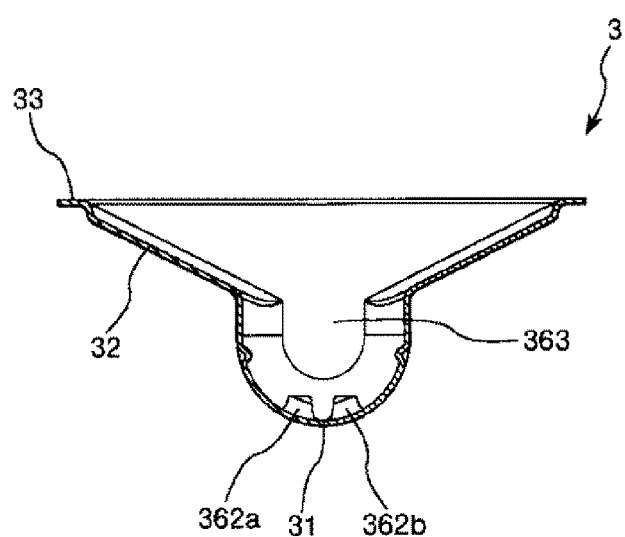
FIG. 3 is a cross-sectional view taken along line A-A in FIG. 2.
Figure 5A:
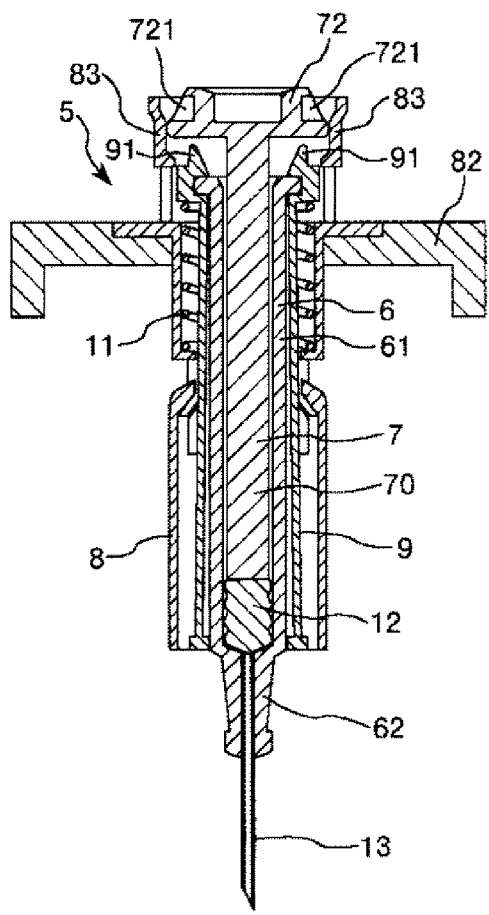
FIGS. 5A and 5B are vertical cross-sectional views of the prefilled syringe of the packaging assembly illustrated in FIG. 1.
Figure 5B:
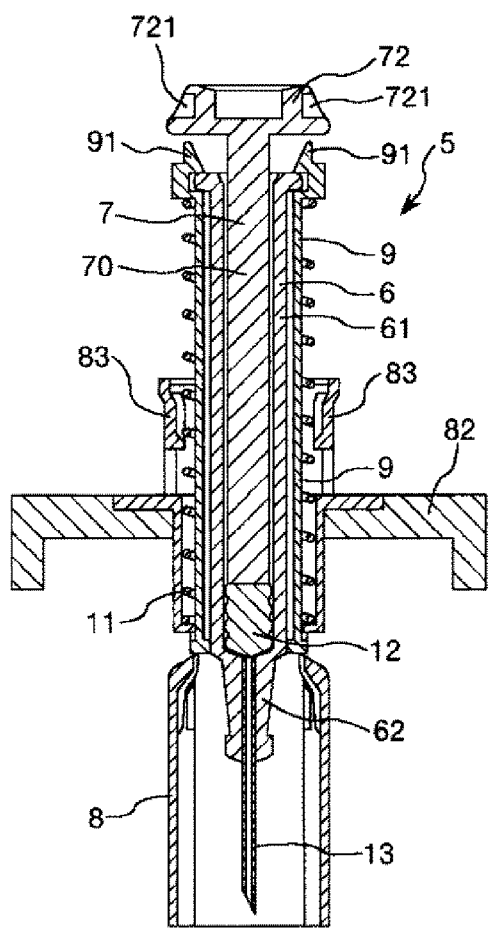
Figure 6:
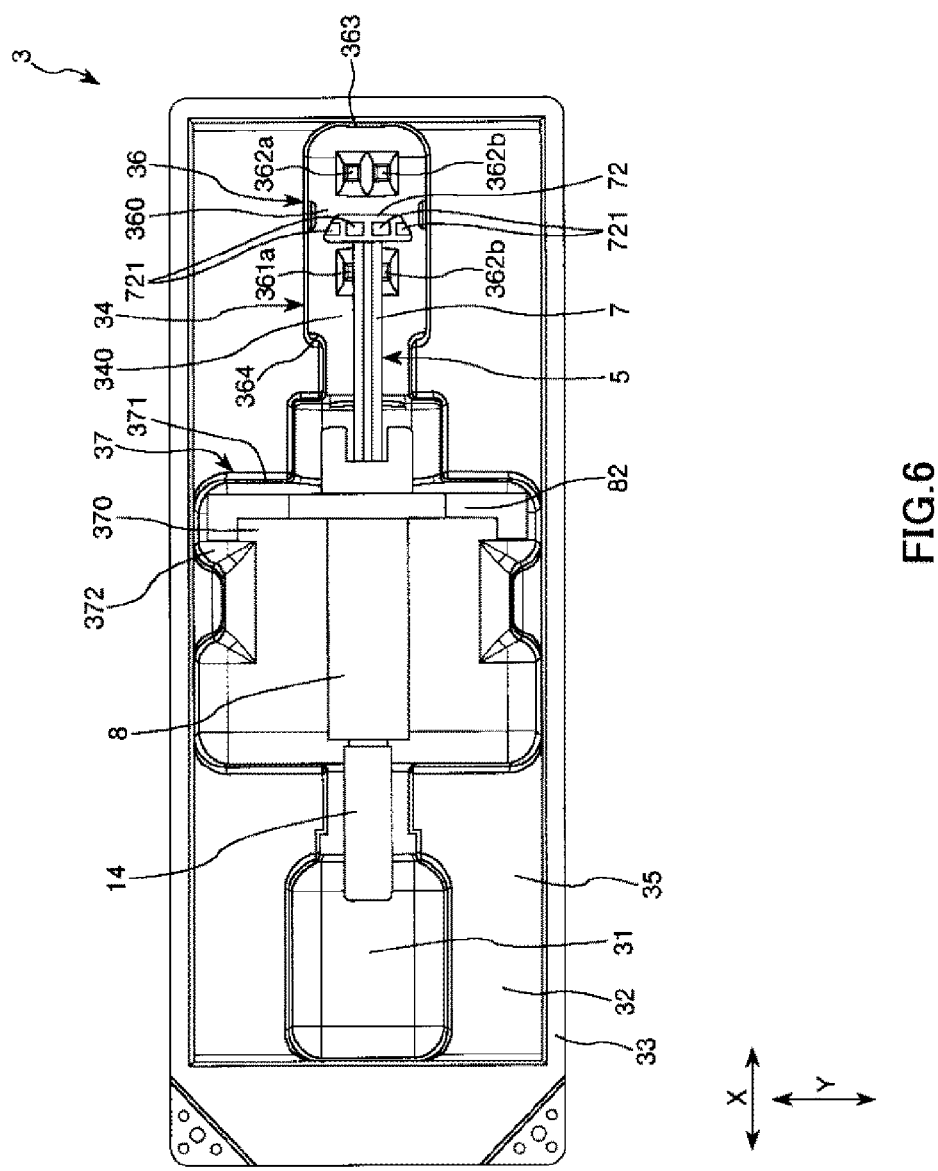
FIG. 6 is a plan view illustrating a state in which a sealing member of the packaging assembly illustrated in FIG. 1 is peeled off.
Figure 7:
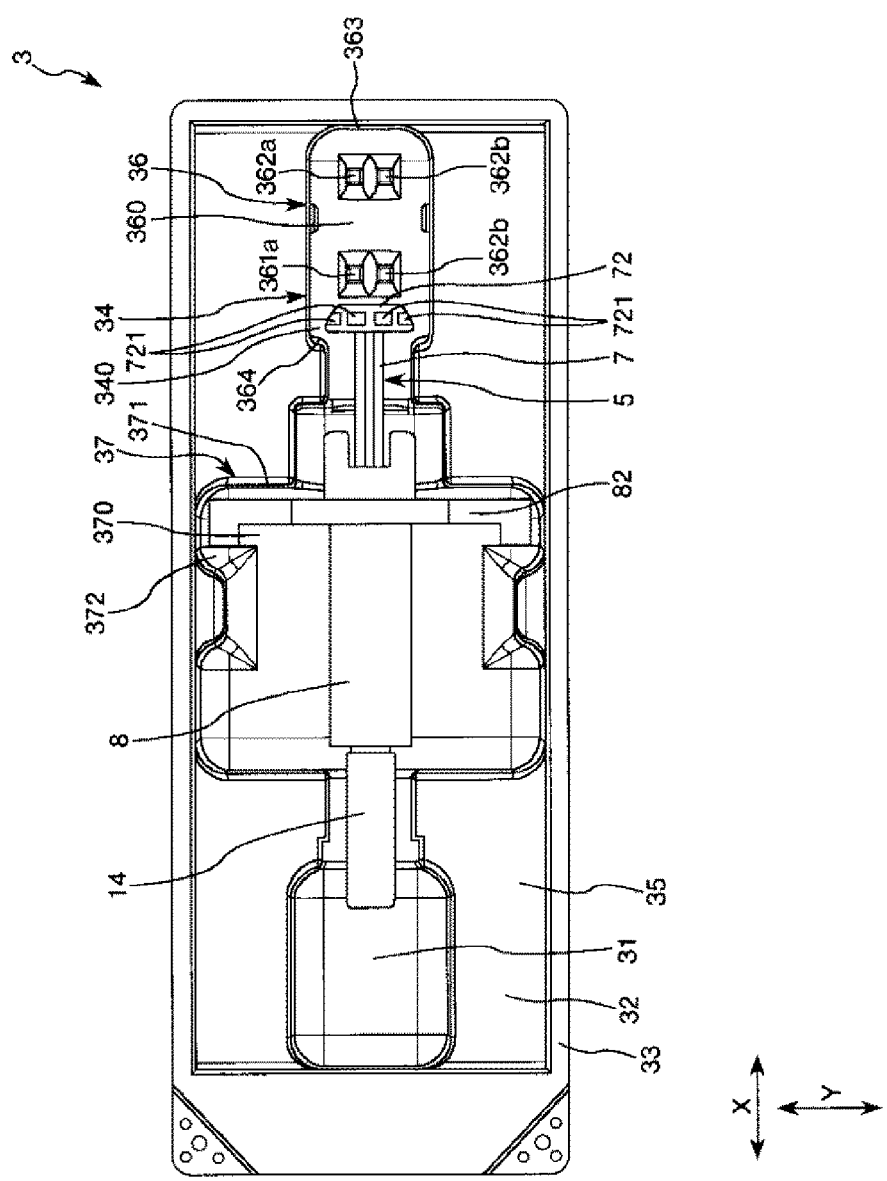
FIG. 7 is a plan view illustrating a state in which a prefilled syringe whose plunger has a protrusion length different from that of the prefilled syringe illustrated in FIG. 6 is housed in the container of the packaging assembly illustrated in FIG. 1.

FIG. 1 is a side view illustrating an embodiment of the packaging assembly of the present invention. FIG. 2 is a plan view of a container of the packaging assembly illustrated in FIG. 1. FIG. 3 is a cross-sectional view taken along line A-A in FIG. 2. Each of FIGS. 4A through 5B is a vertical cross-sectional view of the prefilled syringe of the packaging assembly illustrated in FIG. 1. FIG. 4B is a cross-sectional view taken along line B-B of FIG. 4A, and each of FIGS. 5A and 5B is a cross sectional view corresponding to FIG. 4B. FIG. 6 is a plan view illustrating a state in which a sealing member of the packaging assembly illustrated in FIG. 1 is peeled off. FIG. 7 is a plan view illustrating a state in which a prefilled syringe whose plunger has a protrusion length different from that of the prefilled syringe illustrated in FIG. 6 is housed in the container of the packaging assembly illustrated in FIG. 1.

Incidentally, In the following description, the upper side in FIG. 1 will be referred to as "above" or an "upper side", the lower side will be referred to as "below" or a "lower side", the right side will be referred to as "right" or a "proximal end", and the left side will be referred to as "left" or a "distal end" for the convenience of description. In addition, the front side of the paper surface in FIGS. 2, 6 and 7 will be referred to as "above" or an "upper side", the back side will be referred to as "below" or a "lower side", the right side will be referred to as "right" or a "proximal end", and the left side will be referred to as "left" or a "distal end" for the convenience of description. In addition, the upper side in FIG. 3 will be referred to as "above" or an "upper side", and the lower side will be referred to as "below" or a "lower side", In addition, the upper side of the prefilled syringe in FIGS. 4A through 5B will be referred to as a "proximal end", and the lower side will be referred to as a "distal end" for the convenience of description. In addition, the right side of the prefilled syringe in FIGS. 6 and 7 will be referred to as a "proximal end", and the left side will be referred to as a "distal end" for the convenience of description.

As illustrated in FIGS. 1 and 6, a packaging assembly 1 has a prefilled syringe (hereinafter, simply referred to as a "syringe") 5 and a packaging body 2 that houses the syringe 5.

Figure 4A:
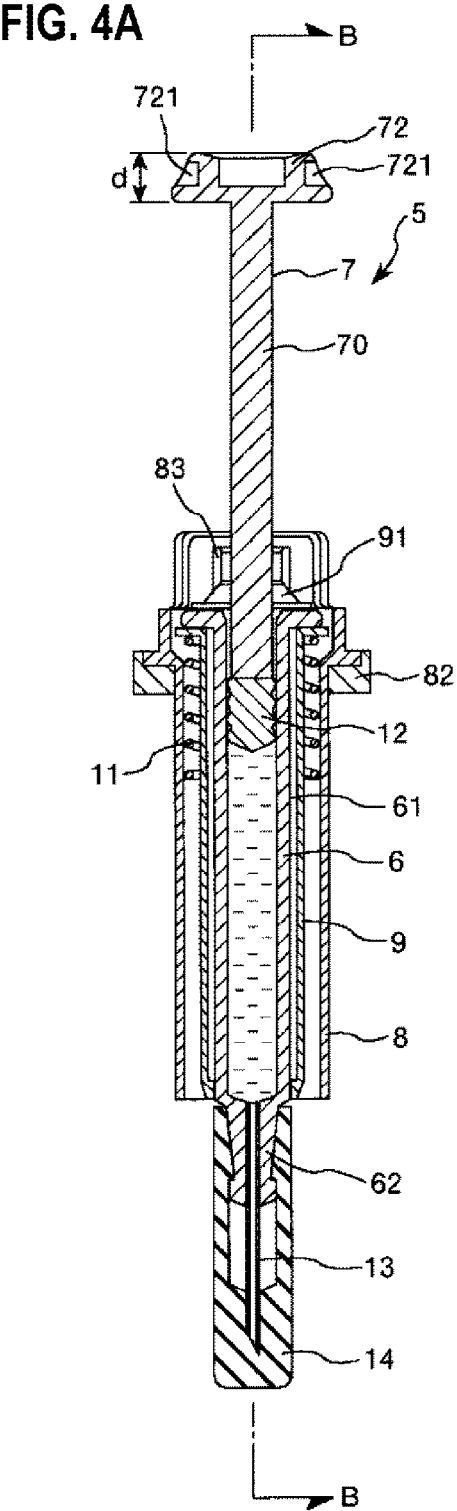
FIGS. 4A and 4B are vertical cross-sectional views of a prefilled syringe of the packaging assembly illustrated in FIG. 1.
Figure 4B:
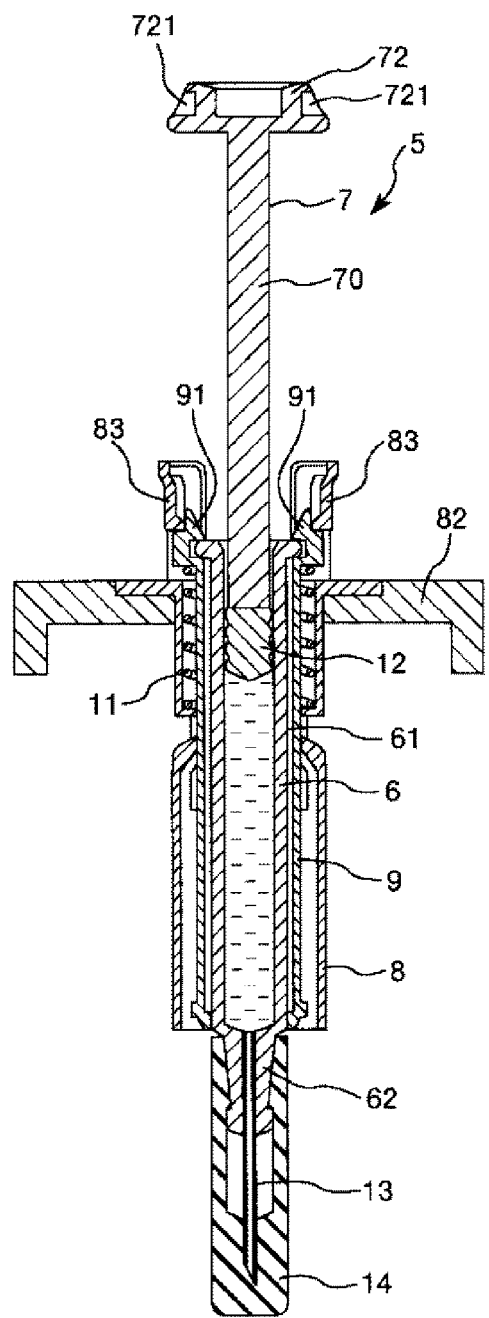

As illustrated in FIGS. 4A, 4B, and 6, the syringe 5 has an elongated shape. The syringe 5 is obtained by housing (filling) a liquid preparation (liquid) such as a drug solution, in advance, inside the syringe 5, and is used at the time of injecting (administering) the liquid preparation into a living body.

Incidentally, the liquid preparation is appropriately selected depending on a purpose of use thereof without being particularly limited, and examples thereof include blood products, saccharide injections such as glucose, electrolyte correction injections such as sodium chloride and potassium lactate, vitamin preparations, vaccine, antibiotic injections, contrast media, steroid agents, protease inhibitors, lipid emulsions, various protein preparations, anticancer agents, anesthetics, stimulants, various drug solutions such as narcotics, various diagnostic agents, and a liquid such as distilled water, physiological saline, a disinfectant, a nutrient, a liquid food, an alcohol.

As illustrated in FIGS. 4A and 4B, the syringe 5 includes: an outer cylinder 6; a gasket 12 slidable in the outer cylinder 6; a plunger 7 provided movably in an axial direction with respect to the outer cylinder 6 and operated to move the gasket 12; a first cylinder body 8 arranged to be concentric with the outer cylinder 6 on the outermost side; a second cylinder body 9 arranged to be concentric with the outer cylinder 6 and the first cylinder body 8 between the outer cylinder 6 and the first cylinder body 8; a coil spring 11; a needle (hollow needle) 13 connected to a cylinder tip 62 of the outer cylinder; and an elastic cap 14 detachably mounted to a cylinder tip 62, which will be described later, of the outer cylinder 6.

The outer cylinder 6 is configured as a bottomed cylindrical member having a bottom portion. The liquid preparation is housed, in advance, in an inner cavity of the outer cylinder 6, that is, a space surrounded by the outer cylinder 6 and the gasket 12, the space positioned on the distal end side of the gasket 12. A position of the plunger 7 with respect to the outer cylinder 6, that is, a protrusion length of the plunger 7 from the outer cylinder 6 differs depending on the amount of the housed liquid preparation. Incidentally, a dimension of the outer cylinder 6 is appropriately set according to the application and various conditions without being particularly limited.

A plate-shaped flange 63 is integrally formed on an outer circumference of a proximal end of the outer cylinder 6. In addition, the cylinder tip 62, which is reduced in diameter with respect to the barrel portion 61 of the outer cylinder 6 and protrudes in a tubular shape, is integrally formed at the center of the bottom portion of the outer cylinder 6.

The needle 13 is attached inside the cylinder tip 62.

The needle 13 is a hollow needle tube and has a sharp needle tip at a distal end thereof, and the living body can be punctured with the needle tip. An inner cavity of the needle 13 communicates with the inner cavity of the outer cylinder 6 and functions as a flow passage through which the liquid preparation from the outer cylinder 6 passes. After puncturing the living body from the skin to a predetermined depth with the needle tip of the needle 13, the liquid preparation is injected into the body via the flow passage of the needle 13.

Incidentally, the cylinder tip 62 and the needle 13 are not limited to those having the above-described configurations. For example, the cylinder tip may be one in which a flow passage through which the liquid preparation can pass is formed, and the needle may be one having a needle hub that can be externally fitted to the cylinder tip such that the needle is provided on the cylinder tip via the needle hub.

Examples of each constituent material of the outer cylinder 6, the first cylinder body 8 and the second cylinder body 9, which will be described later, and the plunger 7 may include various types of resin such as polyvinyl chloride, polyethylene, polypropylene, polystyrene, poly-(4-methyl-pentene-1), polycarbonate, acrylic resin, acrylonitrile-butadiene-styrene copolymers, polyester such as polyethylene terephthalate, butadiene-styrene copolymers, polyamide (for example, nylon 6, nylon 6.6, nylon 6.10, or nylon 12), polyacetal, and cyclic polyolefin.

It is preferable that the constituent materials of the outer cylinder 6, the first cylinder body 8, and the second cylinder body 9 be substantially transparent in order to ensure visibility of each inside.

In addition, it is preferable that a scale (not illustrated) be formed on an outer circumferential surface of the outer cylinder 6. Accordingly, it is possible to determine a liquid amount of the liquid preparation housed in the syringe 1.

The gasket 12 made of an elastic material is housed inside the outer cylinder 6. A plurality of ring-shaped protrusions are formed on an outer circumferential portion of the gasket 12 at predetermined intervals along the axial direction. As the protrusion slides while being in close contact with an inner circumferential surface of the outer cylinder 6, it is possible to reliably maintain liquid tightness and to achieve improvement in sliding.

The constituent material of the gasket 12 is not particularly limited. Examples thereof may include various rubber materials (particularly crosslinked ones) such as natural rubber, isoprene rubber, and butyl rubber and various thermoplastic elastomers based on styrene and polyolefin, and one kind or two or more kinds among them can be mixed and used.

The plunger 7 is connected to the gasket 12. This connecting method is not particularly limited, and for example, there is a method of forming a hollow portion open to a proximal end surface thereof in the gasket 12 and inserting a distal end portion of the plunger 7 into the hollow portion.

The plunger 7 is operated to move the gasket 12 in the longitudinal direction inside the outer cylinder 6.

The plunger 7 includes a main body portion 70 configured using a plate piece whose horizontal section is a cross shape, and a first finger rest 72 is formed integrally with the main body portion 70 at a proximal end thereof. The plunger 7 is operated to move in the distal end direction by pressing the first finger rest 72 with a finger or the like. The first finger rest 72 is formed in a disk shape having a thickness, and a plurality of concave portions 721 are formed along a circumferential direction on an outer circumferential surface thereof (see FIGS. 4A and 4B and the like).

The first cylinder body 8 has a second finger rest 82. The second finger rest 82 is provided on an outer circumference of a proximal end portion of the first cylinder body 8 so as to have a part provided over the circumference thereof and a pair of right and left L-shaped parts protruding from the former part.

When the plunger 7 is operated to move relative to the outer cylinder 6, for example, it is possible to perform the operation by hanging the finger on the second finger rest 82.

In addition, the first cylinder body 8 has a pair of engagement pieces 83 on the proximal end side of the second finger rest 82. The respective engagement pieces 83 are formed in an L shape and are arranged to oppose each other. In addition, the respective engagement pieces 83 are configured to be elastically deformable.

The distal end of the first cylinder body 8 is positioned closer to the proximal end side than the distal end of the outer cylinder 6.

The second cylinder body 9 is provided so as to be movable in the axial direction with respect to the first cylinder body 8. The second cylinder body 9 has a pair of claws 91 at a proximal end portion thereof. The respective claws 91 are arranged to oppose each other. The flange 63 of the outer cylinder 6 is nipped between the pair of claws 91, and the outer cylinder 6 and the second cylinder body 9 are configured to be integrally movable in the axial direction with respect to the first cylinder body 8.

The distal end of the second cylinder body 9 is positioned closer to the proximal end side than the distal end of the outer cylinder 6. In addition, the distal end of the second cylinder body 9 and the distal end of the first cylinder body 8 may be positioned at the same position in the axial direction as in the illustrated configuration or may be positioned at different positions.

The coil spring 11 is installed in a contracted state between the first cylinder body 8 and the second cylinder body 9. The second cylinder body 9 is biased in the proximal end direction with respect to the first cylinder body 8 by the coil spring 11.

In addition, the engagement piece 83 of the first cylinder body 8 is engaged with the claw 91 from the proximal end side in the unused state of the syringe 5, and accordingly, the movement of the second cylinder body 9 in the proximal end direction with respect to the first cylinder body 8 is prevented. Incidentally, a positional relationship between the first cylinder body 8, and the outer cylinder 6 and the second cylinder body 9 is fixed in this state, and thus, the plunger 7 can move relative to the first cylinder body 8.

When using the syringe 5, the elastic cap 14 is removed, the living body is punctured with the needle 13, and the plunger 7 is pressed to move in the distal end direction. Accordingly, the liquid preparation housed in the inner cavity of the outer cylinder 6 is discharged from the needle 13 and injected into the living body. Incidentally, the elastic cap 14 is formed using the same constituent material as the gasket 12, and the needle tip of the needle 13 pierces a distal end portion of the elastic cap 14 and an opening of a proximal end portion is fitted to the cylinder tip 62 in a state where the elastic cap 14 is mounted to the cylinder tip 62 of the outer cylinder 6.

Further, when the plunger 7 moves to the most distal end and the entire liquid preparation housed in the inner cavity of the outer cylinder 6 is discharged as illustrated in FIG. 5A, the first finger rest 72 of the plunger 7 moves between the pair of engagement pieces 83 of the first cylinder body 8 before and after then, and accordingly, the pair of engagement pieces 83 spreads outward so as to be spaced apart from each other. Accordingly, the engagement between the claw 91 of the second cylinder body 9 and the engagement piece 83 is released, and the second cylinder body 9 is moved in the proximal end direction with respect to the first cylinder body 8 by a biasing force of the coil spring 11 together with the outer cylinder 6, the plunger 7, and the gasket 12.

Accordingly, the needle tip of the needle 13 is covered by the first cylinder body 8 as illustrated in FIG. 5B so that it is possible to prevent erroneous puncture by the needle 13 or the like. A safety mechanism is formed of the first cylinder body 8, the second cylinder body 9, the coil spring 11, and the like.

Next, the packaging body 2 will be described.

As illustrated in FIGS. 1 and 2, the packaging body 2 includes a container 3 that houses the syringe 5, and a sealing member 4 detachably attached to the container 3. The sealing member 4 is formed in a sheet shape.

As illustrated in FIGS. 2, 6 and 7, the container 3 has a bottom portion 31, a side wall portion 32 extending upward from the periphery of the bottom portion 31, and a flange portion 33 extending laterally from an upper end of the side wall portion 32 and configured to attach the sealing member 4. Further, a housing space 340 configured to house the syringe 5 is formed in an inner part of the container 3 using the bottom portion 31 and the side wall portion 32, an opening 35 configured to take out the syringe 5 from the housing space 340 is formed at an upper end of the housing space 340, and the syringe 5 is taken out from the housing space 340 through the opening 35. Incidentally, a housing portion 34 is configured by the bottom portion 31, the side wall portion 32, the housing space 340, and the like. Although the container 3 is obtained by blister-molding a resin material such as polyethylene terephthalate in the present embodiment, the present invention is not limited thereto.

In addition, a shape of the container 3 is not particularly limited, but may be an elongated shape having a long axis and a short axis, that is, a substantially rectangular shape in a plan view seen from a vertical direction with respect to the bottom portion 31 (hereinafter, referred to as a plan view) in the present embodiment. A direction of the long axis (a longitudinal direction) in FIG. 2 is represented by "X" and also referred to as an "X direction", and a direction of the short axis is represented by "Y" and also referred to as a "Y direction".

In addition, a shape of the housing portion 34 is not particularly limited, but is an elongated shape in the present embodiment. The longitudinal direction of the bottom portion 31 matches the direction X of the long axis of the container 3.

In addition, the bottom portion 31 has a curved shape to be convex downward as illustrated in FIG. 3.

In addition, a part of the side wall portion 32 on the bottom portion 31 side has a curved shape continuous from the bottom portion 31, and a part thereof on the opening 35 side is inclined such that a length of the housing space 340 in the Y direction gradually increases toward the upper side. With this inclination, it is possible to easily and smoothly insert the finger to the position of the syringe 5 inside the housing portion 34 at the time of taking the syringe 5 out of the housing portion 34, and accordingly, it is easy to take out the syringe 5.

In addition, the flange portion 33 is formed on an outer circumferential portion of an upper end portion of the container 3 over the entire circumference thereof.

An upper surface of the flange portion 33 is a part to which the sealing member 4 can be attached, and the sealing member 4 is detachably attached to the upper surface of the flange portion 33 by, for example, fusion bonding, adhesion, or the like. An end portion of a part corresponding to one of four corners of the container 3 of the sealing member 4 is not attached to the flange portion 33 such that the part can be grasped. The flange portion 33 is covered and the inside of the housing portion 34, that is, the housing space 340 is airtightly sealed by the sealing member 4 so that it is possible to maintain the sterile state of the inside of the packaging body 2.

In addition, when peeling off the sealing member 4 from the packaging body 2, it is possible to easily peel off the sealing member 4 by gripping the part of the sealing member 4 that is not attached to the flange portion 33.

The housing portion 34 is configured so as to be capable of housing the syringes 5 having different protrusion lengths of the plungers 7 from the outer cylinders 6 (hereinafter, simply referred to as "protrusion lengths of the plungers 7"). Hereinafter, the housing portion 34 will be described.

As illustrated in FIGS. 2 and 6, a first finger rest housing portion 36 that houses the first finger rest 72 of the plunger 7 of the syringe 5 is arranged at a right end portion of the housing portion 34. A space inside the first finger rest housing portion 36 is a space capable of housing the first finger rest 72 of the plunger 7 of the syringe 5, that is, a first finger rest housing space 360.

A length L1 of the first finger rest housing space 360 in the X direction is set to be longer than a thickness d of the first finger rest 72. Accordingly, the syringes 5 having the different protrusion lengths of the plungers 7 can be housed in the housing portion 34.

In addition, as illustrated in FIGS. 2 and 3, a plurality of convex portions 361a, 361b, 362a, and 362b (four in the illustrated configuration) are formed on the bottom portion 31 of the first finger rest housing portion 36 as a first regulating portion that regulates the movement of the plunger 7 in the distal end direction in a state where the syringe 5 is housed inside the housing portion 34 (hereinafter, simply referred to also as a "housed state). The convex portion 361a and the convex portion 361b are aligned in the Y direction, and similarly, the convex portion 362a and the convex portion 362b are aligned in the Y direction. Further, the pair of convex portions 361a and 361b and the pair of convex portions 362a and 362b are aligned in the X direction to be spaced apart from each other at a predetermined interval.

In addition, the pair of convex portions 362a and 362b is spaced apart from a right end portion 363 of the side wall portion 32 of the first finger rest housing portion 36 by a predetermined distance.

In addition, the pair of convex portions 361a and 361b is spaced apart from a left end portion 364 of the side wall portion 32 of the first finger rest housing portion 36 by a predetermined distance.

In the housed state, the first finger rest 72 is arranged between the pair of convex portions 361a and 361b and the pair of convex portions 362a and 362b, is arranged between the end portion 363 and the pair of convex portions 362a and 362b, or is arranged between the end portion 364 and the pair of convex portions 361a and 361b. Alternatively, any one pair of convex portions among the pair of convex portions 361a and 361b and the pair of convex portions 362a and 362b is inserted into the concave portions 721 of the first finger rest 72. Accordingly, the syringes 5 having the different protrusion lengths of the plungers 7 can be housed in the housing portion 34, for example, as illustrated in FIGS. 6 and 7. In this case, it is possible the protrusion lengths of the plungers 7 to be in a range of 0.4 to 1.0 mL as, for example, in terms of the amount of the liquid preparation housed in the inner cavity of the outer cylinder 6.

In a case in which the first finger rest 72 is arranged between the pair of convex portions 361a and 361b and the pair of convex portions 362a and 362b as illustrated in FIG. 6, the movement of the plunger 7 in the distal end direction is regulated by the first finger rest 72 abutting on the pair of convex portions 361a and 361b when the plunger 7 tries to move in the distal end direction. In addition, when the plunger 7 tries to move in the proximal end direction, the movement of the plunger 7 in the proximal end direction is regulated by the first finger rest 72 abutting on the pair of convex portions 362a and 362b in the same manner.

In addition, in a case where the first finger rest 72 is arranged between the end portion 363 and the pair of convex portions 362a and 362b, the movement of the plunger 7 in the distal end direction is regulated by the first finger rest 72 abutting on the pair of convex portions 362a and 362b when the plunger 7 tries to move in the distal end direction. In addition, when the plunger 7 tries to move in the proximal end direction, the movement of the plunger 7 in the proximal end direction is regulated by the first finger rest 72 abutting on the end portion 363 in the same manner.

In addition, in a case where the first finger rest 72 is arranged between the end portion 364 and the pair of convex portions 361a and 361b as illustrated in FIG. 7, the movement of the plunger 7 in the distal end direction is regulated by the first finger rest 72 abutting on the end portion 364 when the plunger 7 tries to move in the distal end direction. In addition, when the plunger 7 tries to move in the proximal end direction, the movement of the plunger 7 in the proximal end direction is regulated by the first finger rest 72 abutting on the pair of convex portions 361a and 361b in the same manner.

In a case where the pair of convex portions 361a and 361b is inserted into the concave portions 721 of the first finger rest 72, the movement of the plunger 7 in the distal end direction is regulated by engagement between the pair of convex portions 361a and 361b and the concave portions 721 of the first finger rest 72 when the plunger 7 tries to move in the distal end direction. In addition, when the plunger 7 tries to move in the proximal end direction, the movement of the plunger 7 in the proximal end direction is regulated by the engagement between the pair of convex portions 361a and 361b and the concave portions 721 of the first finger rest 72 in the same manner.

In a case in which the pair of convex portions 362a and 362b is inserted into the concave portions 721 of the first finger rest 72, the movement of the plunger 7 in the distal end direction is regulated by engagement between the pair of convex portions 362a and 362b and the concave portions 721 of the first finger rest 72 when the plunger 7 tries to move in the distal end direction. In addition, when the plunger 7 tries to move in the proximal end direction, the movement of the plunger 7 in the proximal end direction is regulated by the engagement between the pair of convex portions 362a and 362b and the concave portions 721 of the first finger rest 72 in the same manner.

In this manner, syringes 5 having different protrusion lengths of the plungers 7 can be housed in the housing portion 34, and it is possible to inhibit discharge of the liquid preparation from the needle 13 caused by the movement of the plunger 7 in the distal end direction and to inhibit unintentional deployment of the safety mechanism of the syringe 5 described above.

In addition, a length L2 in the X direction of a space between the pair of convex portions 361a and 361b and the pair of convex portions 362a and 362b in the first finger rest housing space 360 is set to be longer than the thickness d of the first finger rest 72. Accordingly, when the first finger rest 72 is arranged between the pair of convex portions 361a and 361b and the pair of convex portions 362a and 362b, the syringes 5 having the different protrusion lengths of the plungers 7 can be housed in the housing portion 34.

Similarly, a length in the X direction of a space between the end portion 364 and the pair of convex portions 361a and 361b is set to be longer than the thickness d of the first finger rest 72.

In addition, a second finger rest housing portion 37 that houses the second finger rest 82 provided on the first cylinder body 8 of the syringe 5 is arranged in the vicinity of the center of the housing portion 34 in the X direction. A space inside the second finger rest housing portion 37 is a space capable of housing the second finger rest 82 of the syringe 5, that is, a second finger rest housing space 370.

In the housed state, the second finger rest 82 is housed inside the second finger rest housing portion 37, that is, is arranged between a right end portion 371 and a left end portion 372 of the side wall portion 32 of the second finger rest housing portion 37.

When the plunger 7 tries to move in the distal end direction, the movement of the plunger 7 in the distal end direction is regulated by the second finger rest 82 abutting on the end portion 372. In addition, when the plunger 7 tries to move in the proximal end direction, the movement of the plunger 7 in the proximal end direction is regulated by the second finger rest 82 abutting on the end portion 371 in the same manner. Therefore, a second regulating portion, which regulates the movement of the first cylinder body 8 in the distal end direction and the proximal end direction in the housed state, is configured by the end portions 371 and 372.

As described above, it is possible to house each of the plurality of syringes 5 having the different protrusion lengths of the plungers 7 from the outer cylinders 6 according to the packaging body 2 and the packaging assembly 1. Accordingly, it is unnecessary to prepare a dedicated packaging body in accordance with the protrusion length of the plunger 7 so that labor is saved, which is economical.

Although embodiments of a packaging body and a packaging assembly have been above, the present invention is not limited thereto, and each portion can be replaced with an a configuration capable of performing the same function. In addition, elements may be added.

In addition, the packaging body has the sealing member that seals the inside of the housing portion of the container in the above-described embodiment, but the present invention is not limited thereto and may be configured to have a housing box to house the container without providing the sealing member. In this case, it is preferable that the housing box house the container in a slidable manner. Incidentally, the packaging body may be configured to include both the sealing member and the housing box.

In addition, the container of the packaging body is not limited to the configuration of the above-described embodiment, but may be formed by, for example, providing a cut or the like on a sheet made of paper or slightly hardened resin and folding the sheet in the present invention.

In addition, the second regulating portion is configured to regulate the movement by abutting on the second finger rest in the above-described embodiment, but the present invention is not limited thereto. The movement may be regulated by, for example, abutting on another part of a member movable with respect to the plunger.

In addition, the prefilled syringe has the safety mechanism in the above-described embodiment, but the present invention is not limited thereto. For example, the prefilled syringe may not necessarily have the safety mechanism.

In addition, the second finger rest is provided in the first cylinder body in the prefilled syringe in the above-described embodiment, but the present invention is not limited thereto. For example, the second finger rest may be provided in the outer cylinder, for example, in the case of not including the above-described safety function.

In addition, the prefilled syringe has the mode in which the liquid is discharged by manually pressing the plunger in the above-described embodiment, but the present invention is not limited thereto, and may be a mode, for example, in which the liquid is discharged by pressing the plunger with a spring or the like, that is, an auto injector or the like.

In addition, the syringe has a configuration in which the drug solution is prefilled inside the syringe in advance in the above-described embodiment, but the present invention is not limited thereto. For example, a drug as a solid preparation such as a powdered preparation may be housed in the syringe. In this case, a liquid such as a solvent is injected into the syringe at the time of use, and a solution formed by dissolving a drug in the liquid can be used as a "drug solution".

A packaging body according to an embodiments is configured to house a prefilled syringe having an outer cylinder fillable with a liquid and a plunger movable with respect to the outer cylinder, and includes a container having a housing portion that houses the prefilled syringe. The housing portion is capable of housing the prefilled syringes with different protrusion lengths of the plungers from the outer cylinders, and has a first regulating portion that regulates movement of the plunger in a distal end direction in a housed state where the prefilled syringe is housed. In addition, a packaging assembly according to an embodiments includes the packaging body; and the prefilled syringe housed in the housing portion. Thus, it is possible to house each of a plurality of prefilled syringes whose plungers have different protrusion lengths from outer cylinders. Accordingly, it is unnecessary to prepare a dedicated packaging body in accordance with the protrusion length of the plunger so that labor is saved, which is economical. Therefore, there is the industrial applicability.

REFERENCE NUMERAL LIST

1 Packaging assembly
2 Packaging body
3 Container
31 Bottom portion
32 Side wall portion
33 Flange portion
34 Housing portion
340 Housing space
35 Opening
36 First finger rest housing portion
360 First finger rest housing space
361a, 361b, 362a, 362b Convex portion
363, 364 End portion
37 Second finger rest housing portion
370 Second finger rest housing space
371, 372 End portion
4 Sealing member
5 Syringe
6 Outer cylinder
61 Body portion
62 Cylinder tip
63 Flange
7 Plunger
70 Main body portion
72 First finger rest
721 Concave portion
8 First cylinder body
82 Second finger rest
83 Engagement piece
9 Second cylinder body
91 Claw
11 Coil spring
12 Gasket
13 Needle
14 Cap
L1, L2 Length
d Thickness
X Long-axis direction
Y Short-axis direction

What is claimed is:

1. A packaging body configured to house a prefilled syringe that comprises an outer cylinder that is fillable with a liquid, a plunger that is movable with respect to the outer cylinder and that comprises a first finger rest at a proximal end of the plunger, the packaging body comprising:
a container comprising a housing portion configured to house the prefilled syringe, wherein the housing portion has an elongated shape,
wherein the housing portion is configured to house the prefilled syringes with various protrusion lengths of the plungers from the outer cylinders, and comprises a first regulating portion configured to regulate movement of the plunger in a distal end direction in a housed state in which the prefilled syringe is housed in the housing portion,
wherein the housing portion comprises a first finger rest housing portion configured to house the first finger rest,
wherein a length of a space of the first finger rest housing portion in a longitudinal direction of the housing portion is larger than a thickness of the first finger rest,
wherein the first regulating portion comprises a plurality of convex portions, at least some of which are arranged along the longitudinal direction of the housing portion,
wherein at least one of the convex portions is insertable into a concave portion of the first finger rest in the housed state.

2. The packaging body according to claim 1, wherein:
the first regulating portion is configured such that the first finger rest is insertable between two adjacent ones of the convex portions that are arranged along the longitudinal direction of the housing portion.

3. The packaging body according to claim 1, wherein:
the housing portion comprises a second regulating portion configured to, in the housed state, regulate movement in the distal end direction and a proximal end direction of a member of the prefilled syringe that is moveable with respect to the plunger.

4. The packaging body according to claim 3, wherein the housing portion comprises a second finger rest housing portion configured to house a second finger rest of the prefilled syringe that is moveable with respect to the plunger.

5. The packaging body according to claim 3, further comprising:
a sealing member configured to attach to a flange portion at an upper end of a side wall of the container and seal the housing portion.

6. A packaging assembly comprising:
a prefilled syringe comprising:
an outer cylinder that is fillable with a liquid, and
a plunger that is movable with respect to the outer cylinder and that comprises a first finger rest at a proximal end of the plunger, wherein the first finger rest comprises a concave portion; and
a packaging body comprising:
a container comprising a housing portion housing the prefilled syringe, wherein the housing portion has an elongated shape,
wherein the housing portion is configured to house the prefilled syringes with various protrusion lengths of the plungers from the outer cylinders, and comprises a first regulating portion that regulates movement of the plunger in a distal end direction,
wherein the housing portion comprises a first finger rest housing portion configured to house the first finger rest,
wherein a length of a space of the first finger rest housing portion in a longitudinal direction of the housing portion is larger than a thickness of the first finger rest,
wherein the first regulating portion comprises a plurality of convex portions, at least some of which are arranged along the longitudinal direction of the housing portion, and
wherein at least one of the convex portions is insertable into a concave portion of the first finger rest in the housed state.

7. The packaging assembly according to claim 6, wherein:
the prefilled syringe comprises a member that is moveable with respect to the plunger, and the housing portion has a second regulating portion that, in the housed state, regulates movement in the distal end direction and a proximal end direction of said member.

8. The packaging assembly according to claim 6, wherein the prefilled syringe comprises a second finger rest that is moveable with respect to the plunger, and
the housing portion includes a second finger rest housing portion configured to house the second finger rest.

9. The packaging assembly according to claim 6, wherein:
the packaging body further comprises a sealing member attached to a flange portion at an upper end of a side wall of the container and seal the housing portion.

\* \* \* \* \*